United States Patent [19]
Roth et al.

[11] Patent Number: 5,763,712
[45] Date of Patent: Jun. 9, 1998

[54] PROCESS FOR THE PREPARATION AND FRACTIONATION OF A MIXTURE OF DIMETHYL ETHER AND CHLOROMETHANE WITH METHANOL AS EXTRACTANT

[75] Inventors: Peter Roth, Eppstein; Erhard Leistner, Braunfels; Wolfgang Wendel, Kelkheim, all of Germany

[73] Assignee: Hoechst Aktiengesellschaft, Germany

[21] Appl. No.: 880,608

[22] Filed: Jun. 23, 1997

[30] Foreign Application Priority Data

Jun. 25, 1996 [DE] Germany ............ 196 25 282.2

[51] Int. Cl.$^6$ .................... C07C 17/00; C07C 41/00
[52] U.S. Cl. ............................. 570/258; 568/698
[58] Field of Search ................. 568/698; 570/258

[56] References Cited

U.S. PATENT DOCUMENTS 3,983,180  9/1976  Habata et al. .................. 260/657

*Primary Examiner*—Gary Geist
*Assistant Examiner*—Jafar Parson
*Attorney, Agent, or Firm*—Connolly & Hutz

[57] ABSTRACT

This invention relates to a process for the preparation and fractionation of a mixture of dimethyl ether and chloromethane by extractive distillation with methanol as extractant. The mixture is prepared by reacting methanol with hydrogen chloride. The mixture is then distilled to remove water and is subsequently subjected to an extractive distillation with methanol as extractant, with chloromethane resulting as top product. In another distillation step, the remaining dimethyl ether is separated from the methanol.

13 Claims, 1 Drawing Sheet

PROCESS FOR THE PREPARATION AND FRACTIONATION OF A MIXTURE OF DIMETHYL ETHER AND CHLOROMETHANE WITH METHANOL AS EXTRACTANT

The present invention relates to a process for the preparation of a mixture of dimethyl ether and chloromethane, and to the fractionation thereof by means of extractive distillation with methanol as extractant.

Chloromethane is industrially important as starting material for the preparation of chlorofluorocarbons which are then used as propellant gases in aerosol packs. Dimethyl ether is increasingly being used as propellant in aerosol packs because it is halogen-free and thus has less potential to degrade ozone.

Both compounds are produced as shown in equations (I) and (II) in the reaction of methanol with HCl, which is frequently carried out industrially on $\gamma\text{-}Al_2O_3$ catalysts to increase the reaction rate:

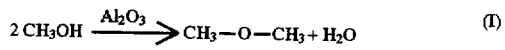

$$2\,CH_3OH \xrightarrow{Al_2O_3} CH_3\!-\!O\!-\!CH_3 + H_2O \quad (I)$$

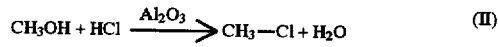

$$CH_3OH + HCl \xrightarrow{Al_2O_3} CH_3\!-\!Cl + H_2O \quad (II)$$

In the previous prior art it was customary to regard the dimethyl ether produced in the preparation of chloromethane as waste, and to dispose of it by hydrolysis with sulfuric acid. However, since dimethyl ether is a valuable product because it can be used as propellant, there was a need for a process which makes it possible to exploit industrially the unavoidable production of dimethyl ether.

The mixture of dimethyl ether and chloromethane cannot be worked up by distillation according to the prior art because the boiling points of the components are very close to one another (dimethyl ether boiling point=−24.9° C., chloromethane boiling point =−23.7° C.), and moreover the components form an azeotrope.

The object was thus to develop a preparation and separation process which makes it possible to produce both pure dimethyl ether and pure chloromethane.

This object has been achieved according to the invention by a two-stage synthetic process with subsequent three-stage workup process, the workup comprising an extractive distillation with methanol. The invention thus relates to a process for the preparation and fractionation of a mixture of dimethyl ether and chloromethane, which comprises a) reacting methanol with an excess of HCl,
b) reacting the mixture obtained in step a) with an excess of methanol,
c) feeding the mixture obtained in step b) to a first distillation column,
d) taking off water from the bottom product from the first distillation column,
e) taking off the mixture containing methanol, dimethyl ether and chloromethane which emerges at the top of the first distillation column,
f) feeding the mixture obtained in step e) to an extractive distillation column,
g) adding methanol as extractant in the upper part of the extractive distillation column,
h) taking off a mixture of methanol and dimethyl ether from the bottom product of the extractive distillation column,
i) drawing off chloromethane from the top of the extractive distillation column,
k) feeding the mixture taken off in step h) to a second distillation column,
l) taking off methanol from the bottom product of the second distillation column,
m) taking off dimethyl ether at the top of the second distillation column,
n) feeding part of the methanol obtained in step l) into the reactions described in steps a) and b), and
o) feeding the remaining part of the methanol obtained in step l) to the addition, described in step g), of methanol into the upper part of the extractive distillation column.

It is preferred to use a catalyst for the esterification reaction described in steps a) and b). Suitable examples are $\gamma\text{-}Al_2O_3$ catalysts.

Delivery of the mixture described in step c) preferably takes place by liquefying the mixture, which results as a gas, in a condenser, delivering the condensate with a pump and vaporizing it again before entry into the first distillation column.

The extractive distillation is preferably carried out under pressures between 1 and 25 bar. All the columns used can be of any suitable design, and packed columns are preferably used.

In one embodiment of the invention, part of the product stream obtained in step m) is taken off and fed into the reaction described in steps a) and b). This embodiment allows the ratio of the amounts of chloromethane and dimethyl ether produced to be influenced by shifting the equilibrium.

Figure 1:
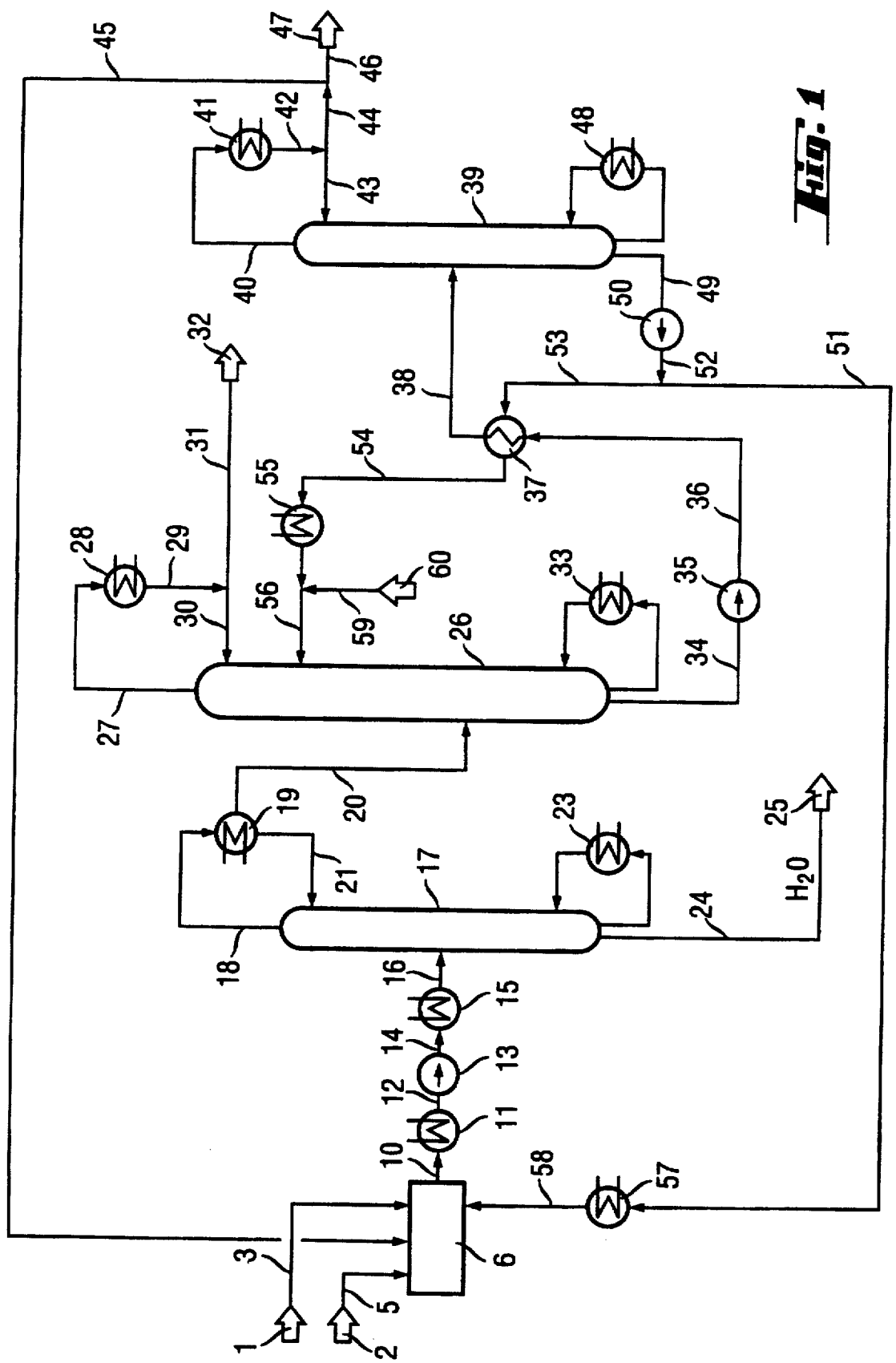
FIG. 1 shows a flow diagram for a preferred embodiment of the process according to the invention, which is explained in detail hereinafter.

Methanol (1) vapor is fed through line (3) into a two-stage esterification reactor (6). In addition, gaseous HCl (2) is fed through line (5) into the reactor (6). The two-stage esterification reactor can be designed in the form of a two-stage tubular reactor. In the first stage, HCl and methanol are added to the reactor. The amounts of the reactants are such that the amount of substance for HCl is up to 20% above the amount of substance stoichiometrically necessary for reaction with the methanol. The mixture of HCl and methanol flows through the first stage of the reactor, which may be charged with a catalyst. In the case of a gas-phase reaction, the reaction is exothermic so that cooling should be provided for both stages of the reactor. The mixture of chloromethane, water and HCl leaving the first stage of the reactor is mixed with an amount of methanol which is up to 20% above the amount of substance stoichiometrically necessary for reaction with the HCl contained in the mixture. The mixture flows through the second stage of the reactor, which may likewise be charged with a catalyst. The reaction can be carried out with liquid or gaseous reactants. The reactions indicated in equations (I) and (II) take place in the reactor (6). The resulting reaction mixture, which consists of dimethyl ether, chloromethane, water and methanol, leaves the reactor (6) through line (10) and can be condensed in the condenser (11). From there it passes through line (12) to the pump (13) and then through line (14) to the vaporizer (15). The vaporized reaction mixture is fed through line (16) into the first distillation column (17). The water (25) of reaction is separated from the other components, that is to say dimethyl ether, chloromethane and methanol, in the first distillation column (17). The water (25) of reaction is the bottom product in the first distillation column (17) and is drawn off through line (24). The vapor, consisting of dimethyl ether, chloromethane and methanol, which is the top product from the first distillation column (17) passes through line (18) where appropriate into the condenser (19). Part of the top product from the first distillation column (17) can be returned through line (21) to the top of the first distillation column (17), and the remaining part passes through line (20) to the extractive distillation column (26). Alternatively, the product stream can also be fed as vapor into the extractive distillation column (26). Separation of dimethyl ether and chloromethane takes place in the extractive distillation column (26). Methanol is added as extractant through line (56) in the upper part of the extractive distillation column (26). It is preferred to add methanol at a temperature of from 5 to 50° C. Dimethyl ether dissolves in methanol and is deposited in the bottom product. The bottom product, consisting of dimethyl ether and methanol, from the extractive distillation column (26) is fed through line (34), pump (35), line (36), where appropriate the heat exchanger (37) and line (38), into the second distillation column (39). The top product taken off from the extractive distillation column (26) through line (27) is pure chloromethane, which can be liquefied in the condenser (28). This top product is drawn off through line (29) and can in part be returned through line (30) to the extractive distillation column (26), otherwise all of it, or some of it, is fed through line (31) to the product store (32). Separation of dimethyl ether and methanol takes place in the second distillation column (39). The top product from the second distillation column (39) is pure dimethyl ether. This can be fed through line (40) to the condenser (41). This top product can in part be returned through lines (42) and (43) to the second distillation column (39), otherwise all of it, or part of it, is fed through lines (42), (44) and (46) to the product store (47).

Alternatively, a dimethyl ether part-stream can be fed from line (44) through line (45) into the esterification reactor (6). Charging of the esterification reactor (6) with dimethyl ether makes it possible to change the ratio of the dimethyl ether and chloromethane products by influencing the equilibrium.

The bottom product from the second distillation column (39) is pure methanol. It is fed through line (49) to a pump (50) and from there through line (52) partly through line (51) to the vaporizer (57), and is fed through line (58) into the esterification reactor (6). The other methanol part-stream is fed through line (53), where appropriate the heat exchanger (37), line (54), the cooler (55) and line (56) into the upper part of the extractive distillation column (26). Fresh methanol (60) is fed into the system through line (59) to compensate for losses. The bottom products from the three distillation columns (17), (26) and (39) are each heated with the vaporizers (23), (33) and (48).

The following table summarizes the top and bottom temperatures occurring in the columns in the preferred pressure range (temperatures in °C).

| Column | 1 bar | | 25 bar | |
|--------|-------|--------|--------|--------|
|        | Top   | Bottom | Top    | Bottom |
| (17)   | −20   | 100    | 70     | 224    |
| (26)   | −24   | 80     | 90     | 180    |
| (39)   | −25   | 64     | 85     | 180    |

EXAMPLE 7.1 th methanol and 5.3 th HCl are fed into an esterification reactor (6). The two-stage reaction at 250° C. under a pressure of 4 bar using a γ-$An_2O_3$ catalyst produces a reaction gas of the following composition:

dimethyl ether: 1.8 th
methanol: 0.01 th
chloromethane: 7.3 th
$H_2O$: 3.29 th

This reaction gas is completely liquefied in a condenser (11) under about 4 bar and at a minimum temperature of about 10° C. The resulting condensate is delivered by pump (13) into the vaporizer (15).

The condensate is partially vaporized here under 10 bar and at about 100° C. It is possible to use as heating medium for this purpose the heat of condensation liberated in the condenser (11). The vapor/liquid mixture from the vaporizer (15) is completely fed into the first distillation column (17). The latter is likewise operated under a pressure of about 10 bar and with a top temperature of 45° C. and a bottom temperature of 177° C. The bottom product consists of about 3.3 th water (25) of reaction. The water of reaction is free of the other products and can be fed into a biological water treatment. The top product vapor downstream of the condenser (19) thus consists of:

dimethyl ether: 1.8 th
methanol: 0.01 th
chloromethane: 7.3 th
with a small amount of water (about 5 ppm $H_2O$).

It is fed through line (20) into the extractive distillation column (26). The dimethyl ether is dissolved in 42 th methanol as extractant therein. Since a certain amount of chloromethane also dissolves in the extractant, it is stripped off in the lower part of the extractive distillation column (26). Heating steam from the vaporizer (33) can be used for bottom heating. The bottom product from the extractive distillation is a mixture consisting of

| 1.8 t/h  | dimethyl ether |
| 42 t/h   | extraction methanol |
| 0.01 t/h | methanol excess from the reaction. |

The bottom product contains about 1 ppm chloromethane. The top product from the extractive distillation column (26) is 7.3 th chloromethane with a dimethyl ether content of less than 20 ppm. The extractive distillation column (26) is likewise operated under a pressure of 10 bar. The extraction methanol must be fed in as cold as possible, preferably at about 35° C., through line (56). The top temperature of the extractive distillation column (26) is about 40° C., which makes it possible to condense the top product using recycled cooling water. The bottom temperature is about 124° C., so that heating with low pressure steam is possible.

The discharge from the bottom of the extractive distillation column (26) is, with the aid of the pump (35), preheated in the heat exchanger (37) and fed into the second distillation column (39). This column is also operated under 10 bar. The top product is about 1.8 th liquid dimethyl ether at about 40° C. The content of chloromethane in the dimethyl ether is less than 20 ppm.

The bottom product from the second distillation column (39) has a temperature of 132° C. and is pure methanol with less than 20 ppm dimethyl ether. It consists of the "extraction methanol" and the "excess methanol" from the reaction. The "excess methanol" (0.01 th) is returned to the reaction through line (51), while the "extraction methanol" is cooled in the heat exchangers (37) and (55) in order to be fed anew through line (56) into the extractive distillation column (26).

What is claimed is:

1. A process for the preparation and fractionation of a mixture of dimethyl ether and chloromethane, which comprises a) reacting methanol with an excess of HCl, b) reacting the mixture obtained in step a) with an excess of methanol, c) feeding the mixture obtained in step b) to a first distillation column, d) taking off water from the bottom product from the first distillation column, e) taking off the mixture containing methanol, dimethyl ether and chloromethane which emerges at the top of the first distillation column, f) feeding the mixture obtained in step e) to an extractive distillation column, g) adding methanol as extractant in the upper part of the extractive distillation column, h) taking off a mixture of methanol and dimethyl ether from the bottom product of the extractive distillation column, i) drawing off chloromethane from the top of the extractive distillation column, k) feeding the mixture taken off in step h) to a second distillation column, l) taking off methanol from the bottom product of the second distillation column, m) taking off dimethyl ether at the top of the second distillation column, n) feeding part of the methanol obtained in step l) into the reactions described in steps a) and b), and o) feeding the remaining part of the methanol obtained in step l) to the addition, described in step g), of methanol into the upper part of the extractive distillation column.

2. The process as claimed in claim 1, wherein part of the product stream obtained in step m) is fed into the reactions described in steps a) and b).

3. The process as claimed in claim 1, wherein the top products obtained in steps i) and m) are condensed before further use thereof.

4. The process as claimed in claim 1, wherein the mixture obtained in step e) is condensed and fed in liquid phase to further processing.

5. The process as claimed in claim 1, wherein the reaction mixture produced as gas during the feeding described in step c) is first condensed and then vaporized again.

6. The process as claimed in claim 1, wherein the extractive distillation taking place after step f) is carried out under pressures between 1 and 25 bar.

7. The process as claimed in claim 1, wherein all the columns used are designed as packed columns.

8. The process as claimed in claim 1, wherein in step g), the extraction methanol is fed at a temperature between 5° and 50° C. into the extractive distillation.

9. The process as claimed in claim 1, wherein the mixture described in step k) is heated before addition to the second distillation column, and wherein the methanol mentioned in step o) is cooled before addition to the extractive distillation column.

10. The process as claimed in claim 9, wherein the heating of the mixture described in step k) takes place in a heat exchanger, and wherein the cooling of the methanol mentioned in step o) likewise takes place in the heat exchanger, and wherein the methanol is brought to a temperature which is as low as possible in a cooler.

11. The process as claimed in claim 1, wherein the reaction described in steps a) and b) is carried out with the aid of a catalyst.

12. The process as claimed in claim 1, wherein the excesses of precursors mentioned in steps a) and b) are up to 20% of the stoichiometric amounts required for the reaction.

13. The process as claimed in claim 1, wherein 1) part of the mixture obtained in step e) is returned to the top of the first distillation column, and/or 2) the product obtained in step i) is partly returned to the top of the extractive distillation column, and/or 3) part of the product obtained in step m) is returned to the top of the second distillation column.

* * * * *

UNITED STATES PATENT AND TRADEMARK OFFICE
CERTIFICATE OF CORRECTION

PATENT NO. : 5,763,712
DATED : June 9, 1998
INVENTOR(S) : Peter Roth, et al

It is certified that error appears in the above-identified patent and that said Letters Patent is hereby corrected as shown below:

In column 3, at line 64, " th " should read -- t/h --; both occurrences.

In column 3, at line 66, " $\gamma\text{-An}_2\text{O}_3$ " should read -- $\gamma\text{-Al}_2\text{O}_3$ --

In column 4, at lines 1, 2, 3, 4, 16, 20, 21, 22, 25, 40, 53 and 60, " th " should read -- t/h --; at all occurrences.

Signed and Sealed this

Thirteenth Day of October 1998

*Attest:*

*Attesting Officer*

BRUCE LEHMAN

*Commissioner of Patents and Trademarks*